United States Patent
Lien et al.

(10) Patent No.: US 11,046,998 B2
(45) Date of Patent: Jun. 29, 2021

(54) PREDICTING THE ABILITY OF ATLANTIC SALMON TO UTILIZE DIETARY PIGMENT BASED ON THE DETERMINATION OF POLYMORPHISMS

(71) Applicant: AquaGen As, Trondheim (NO)

(72) Inventors: Sigbjorn Lien, Aas (NO); Marte Sodeland, Matredal (NO); Thomas Moen, As (NO)

(73) Assignee: AQUAGEN AS, Trondheim (NO)

( * ) Notice: Subject to any disclaimer, the term of this patent is extended or adjusted under 35 U.S.C. 154(b) by 0 days.

(21) Appl. No.: 15/317,302

(22) PCT Filed: Jun. 10, 2015

(86) PCT No.: PCT/GB2015/051713
§ 371 (c)(1),
(2) Date: Dec. 8, 2016

(87) PCT Pub. No.: WO2015/189617
PCT Pub. Date: Dec. 17, 2015

(65) Prior Publication Data
US 2017/0114399 A1    Apr. 27, 2017

(30) Foreign Application Priority Data
Jun. 10, 2014 (GB) .................................... 1410328

(51) Int. Cl.
*C12Q 1/68* (2018.01)
*C12P 19/34* (2006.01)
*C12Q 1/6827* (2018.01)

(52) U.S. Cl.
CPC ..... *C12Q 1/6827* (2013.01); *C12Q 2600/124* (2013.01); *C12Q 2600/156* (2013.01)

(58) Field of Classification Search
CPC ............ C12Q 1/6827; C12Q 2600/124; C12Q 2600/156
See application file for complete search history.

(56) References Cited

FOREIGN PATENT DOCUMENTS

WO       2015189617 A1    12/2015

OTHER PUBLICATIONS

GenBank Locus HF543833, Salmo salar mRNA for beta-carotene 15,15'-monooxygenase 1 like (bcmo1 like gene, (Nov. 21, 2012), from www.ncbi.nlm.nih.gov/nuccore/HF543833.1 (Year: 2012).*
Pennisi, E. A closer look at SNPs suggests difficulties, Science; Sep. 18, 1998; 281, 5384, p. 1787-1789 (Year: 1998).*
Lucentini, J. The Scientist, Dec. 20, 2004, p. 20. (Year: 2004).*
Hacker, U.T. et al. Gut (1997) 40:623-627. (Year: 1997).*
E G Boulding et al.: "Conservation genomics of Atlantic salmon: SNPs associated with QTLs for adaptive traits in parr from four trans-Atlantic backcrosses", Heredity, vol. 101, No. 4, Jul. 23, 2008 (Jul. 23, 2008), pp. 381-391, XP055210752.
Sigbja RN Lien et al.: "A dense SNP-based linkage map for Atlantic salmon (*Salmo salar*) reveals extended chromosome homeologies and striking differences in sex-specific recombination patterns", BMC Genomics, BIOMED Central LTD, London, UK, vol. 12, No. 1, Dec. 19, 2011 (Dec. 19, 2011), p. 615, XP021093244.
Marte Sodeland et al.: "Genome-wide association testing reveals quantitative trait loci for fillet texture and fat content in Atlantic salmon", Aquaculture, vol. 408-409, Sep. 1, 2013 (Sep. 1, 2013), pp. 169-174, XP055209502.
Luigi Ferrucci et al.: "Common Variation in the [beta]-Carotene 15,15'-Monooxygenase 1 Gene Affects Circulating Levels of Carotenoids: A Genome-wide Association Study", The American Journal of Human Genetics, vol. 84, No. 2, Feb. 1, 2009 (Feb. 1, 2009), pp. 123-133, XP055209432.
Helgeland Hanna et al.: "The evolution and functional divergence of the beta-carotene oxygenase gene family in teleost fish-Exemplified by Atlantic salmon", Gene, vol. 543, No. 2, Feb. 26, 2014 (Feb. 26, 2014), pp. 268-274, XP028650024.
Norwegian Industry Standard for Fish, Quality grading of farmed salmon, Standard No. NBS 10-01, Version 2, Year of publication: 1999, 4 pages.
Jimari et al., Genome-Wide Linkage Disequilibrium from 100,000 SNPs in the East Finland Founder Population, Twin Research and Human Genetics, vol. 8, No. 3, pp. 185-197.
Baldan et al., ATP-binding cassette transporter G1 and lipid homeostasis, Curr Opin Lipidol 17:227-232. © 2006 Lippincott Williams & Wilkins.
Lietz et al., Molecular and dietary regulation of β,β-carotene 15,150-monooxygenase 1 (BCMO1), Archives of Biochemistry and Biophysics 502 (2010) 8-16.
Le Bihan-Duval E, Nadaf J, Berri C, Pitel F, Graulet B, et al. (2011) Detection of a Cis eQTL Controlling BMCO1 Gene Expression Leads to the Identification of a QTG for Chicken Breast Meat Color. PLoS One 6(7): e14825. doi:10.1371/journal.pone.0014825.
Jlali et al., A mutation in the promoter of the chicken β,β-carotene 15,15'-monooxygenase 1 gene alters xanthophyll metabolism through a selective effect on its mRNA abundance in the breast muscle, J. Anim. Sci. 2012.90:4280-4288, doi:10.2527/jas2012-5240.

(Continued)

*Primary Examiner* — Stephen T Kapushoc
(74) *Attorney, Agent, or Firm* — Shook, Hardy & Bacon LLP

(57) ABSTRACT

A method of predicting the ability of a salmon to utilise dietary pigment, the method comprising determining the alleles present at one or more DNA polymorphism in the salmon and predicting the ability of the salmon to utilise dietary pigment based on the determination of the alleles. The method may be used for selecting a salmon for use as broodstock. Also contemplated is a method of improving the ability of a salmon to utilise dietary pigment, the method including the step of administering an agent that inhibits the expression of the genes bcmo1-like and/or bcmo1 and/or an agent that inhibits the activities of the proteins Bcmo1-like and/or Bcmo1.

7 Claims, 2 Drawing Sheets
Specification includes a Sequence Listing.

(56) References Cited

OTHER PUBLICATIONS

Telbisz et al., Effects of the lipid environment, cholesterol and bile acids on the function of the purified and reconstituted human ABCG2 protein, Biochem. J. (2013) 450, 387-395 (Printed in Great Britain) doi:10.1042/BJ20121485.
Davidson et al., Sequencing the genome of the Atlantic salmon (*Salmo salar*), Genome Biology 2010, 11:403. http://genomebiology.com/2010/11/9/403.
Hendrickson et al., β-Carotene 15,15'-monooxygenase 1 single nucleotide polymorphisms in relation to plasma carotenoid and retinol concentrations in women of European descent, Am J Clin Nutr 2012;96:1379-89. Printed in USA. © 2012 American Society for Nutrition.
International Search Report and Written Opinion received for PCT Patent Application No. PCT/GB2015/051713, dated Sep. 11, 2015, 10 pages.
International Preliminary Report on Patentability received for PCT Patent Application No. PCT/GB2015/051713, dated Dec. 22, 2016, 8 pages.

\* cited by examiner

PREDICTING THE ABILITY OF ATLANTIC SALMON TO UTILIZE DIETARY PIGMENT BASED ON THE DETERMINATION OF POLYMORPHISMS

The present invention relates to methods for predicting the ability of a salmon to utilise dietary pigment, more specifically the invention relates to predicting the ability of a salmon to utilise dietary pigment by the analysis of DNA polymorphisms.

Consumers of salmon have a preference for fish that can be prepared as a fillet that is deep red in colour in its raw (eg un-cooked) and fresh state, as well as in processed products. The fillet of a salmon (being a single side of the body of a fish, with the bones removed) is mostly composed of muscle tissue. It is the colour of this muscle tissue in the fillet that provides the deep red colour that is most prized by consumers. As a result, salmon that provides a fillet that is deep red in colour are more easily sold and can be sold for a higher price than salmon with fillets of a paler more pink colour. Salmon producers are therefore incentivised to rear salmon with the above-mentioned desired deep red fillet colour.

The red colour of the salmon fillet is caused by dietary carotenoids, in particular astaxhanthin, and (to a lesser extent) canthaxanthin. The pigments responsible for the red colour in wild salmonid fish originate from their natural feeding on small crustaceans. The pigments are catabolised in the liver, forming metabolites that are excreted from the body. However, a fraction of the ingested pigment is deposited in muscle tissue rather than being catabolised. The pigments causing the red colour of salmon tissue is not a natural part of the diets fed to farmed salmon, so the carotenoids, most importantly astaxhanthin, is therefore added to the commercial feed so that the salmon can obtain the red colour wanted by consumers. Salmon farmers use this technique to ensure that the intensities of the red colour of the salmon fillets are high enough to meet their customers' demands, as well as the quality standards of the industry. Norwegian Atlantic salmon farmers, for example, have agreed upon lower limits of the red colour intensity (Industry Standards for Fish, 1999); batches of salmon having a red fillet colour intensity below this lower limit are deemed to be unfit for the consumer market.

The addition of pigments to a salmon's diet adds a significant cost to the production of the salmon; the cost of providing the pigment for the life of an average fish (weighing about 5.5 kg at slaughter) is estimated to represent 2-3% of the total production cost per kg of fish. Reducing the amount of pigment required, whilst still being able to rear salmon with the desired fillet colour, would have a significant impact on the profits of salmon farming. Hence, the salmon producers are interested in rearing salmon that are inherently efficient at retaining the dietary pigments. The salmon producers are also interested in rearing salmon that are inherently (i.e. genetically) similar in their ability to retain the dietary pigments, in order to ensure that all their salmon have a high enough red fillet colour intensity, while at the same time avoiding the unnecessary expenditure relating to pigments on those animals that would in any case easily meet the fillet colour intensity threshold.

One approach towards increasing the redness of the salmon fillets and/or reducing amount of pigment added to the feed is to select salmon as broodstock on the basis of their fillet colour, thereby enabling the development of a population of salmon that present the desired fillet colour even when the diet contains relatively small doses of astaxanthin. The redness of the salmon fillet is determined by many factors, such as the amount of astaxanthin in the feed and the age/body size of the fish. However, genetic disposition is a major determinant of the fillet colour, typically responsible for around 40% of the total variation found in muscle pigment content or red colour intensity. Genetic selection for increased redness can therefore make it possible for producers to obtain, on average, significantly higher red colour intensities and/or a significant decrease in the amount of feed pigment required to reach a certain intensity. Genetic selection will also lead to a reduced variation, within the salmon stock in question, in the ability to obtain the required red colour intensities.

In order to establish fillet colour, the skilled person can measure pigment concentration in the muscle of the salmon by high-pressure liquid-chromatography (HPLC). However, such a method is time-consuming and costly, and requires the sacrifice of the animal. The fillet colour can be evaluated (1) by visual (ie by eye) comparison against the Roche SalmoFan®, (2) by automated inspection of digital photographs, or (3) by using automated systems for objective estimation of pigment concentration based on spectroscopy. Experimental measurements obtained using any of the three last-mentioned methods may be translated to units of pigment content (mg pigment per kg fillet) by correlating, in a sample of at least 50 animals, the measurements in question with HPLC-obtained pigment-content. As a rule of thumb, producers generally aim for an average pigment concentration of above 7 mg per kg fillet, corresponding to Roche SalmoFan® measurements at around 26.

The drawback of the above-mentioned methods for estimating the intensity of the red colour in salmon fillets is that they all require that the salmon first be slaughtered and the fillet prepared. This not only reduces the number of salmon that can be used to form the population of the broodstock, but also means that it is the siblings of the salmon that have been analysed that are used as broodstock. The accuracy of selection is reduced when selection is performed on the basis of phenotypes that are not recorded on the selection candidates, meaning that the population of salmon created from the broodstock may not possess the desired fillet colour that was presented by the tested animals.

There is therefore a need for alternative methodologies for predicting the ability of a salmon to utilise dietary pigment, thereby enabling the selection of salmon that have a greater than normal ability to utilise dietary pigment, and also the deselection of salmon that have a lesser than normal ability to utilise dietary pigment.

The inventors of the present application have, following extensive experimentation, identified that one can predict a salmon's ability to utilise dietary pigment by analysis of one or more DNA polymorphism. Predicting such an ability on the basis of DNA polymorphisms means that analysis can be carried out on a small tissue sample of the salmon and that one does not need to sacrifice the salmon being analysed. Consequently, one can develop a population of salmon directly from broodstock that have been analysed by the new DNA based method (ie marker-assisted selection). It has been found that salmon belonging to a population selected by this method to have a better than normal ability to utilise dietary pigment not only present the desired red colour of fillet when fed a normal level of dietary pigment (assuming other conditions are normal), but may also demonstrate an ability to present this colour of fillet when fed on lesser levels of dietary pigment when normal salmon would be expected to present pale fillets.

Accordingly, in a first aspect of the present invention, there is provided a method of predicting the ability of a salmon to utilise dietary pigment, the method comprising determining the alleles present at one or more DNA polymorphism in the salmon and predicting the ability of the salmon to utilise dietary pigment based on the determination of the alleles.

The utilisation of pigment by salmon is the process of depositing and retaining the dietary pigment in the muscle tissue rather than catabolising and excreting it. The greater the percentage of total dietary pigment that can be extracted from the total dietary pigment and retained in muscle tissue, the greater the ability the salmon has at utilising pigment (and vice versa). The greater the utilisation of pigment the more intense red colour will be presented by the salmon fillet when compared to a fillet produced by a similar salmon (e.g. weight and/or age) with a poorer level of utilisation of pigment and when both fish are fed the same level of dietary pigment. Apart from practising the present invention, the relative level of utilisation of pigment of a test salmon may be confirmed by analysis of the colour of the fillet (for example, by using any of the methods described above) and/or the amount of pigment in a fillet (optionally expressed as mg of pigment per kg of fillet), and comparing that level to that derived from a population of salmon that are fed on a diet that includes the same or substantially the same amount of pigment as that of the test salmon.

Salmon that have a greater than normal ability to utilise dietary pigment are ideal broodstock as they will be able to maximise on the use of pigment in their diet in order to present the desired intense red colour for their fillets. Salmon with a lesser than normal ability to utilise dietary pigment would not ideally be selected as broodstock.

Consequently, the method of the present invention may predict a salmon that has a greater or a lesser than normal ability to utilise dietary pigment based on the determination of the alleles present at one or more DNA polymorphism in the salmon.

For the avoidance of doubt, a salmon that has a greater (or lesser) than normal ability to utilise dietary pigment is most likely to have a muscle pigment content (and hence, a red colour intensity) which is higher (or lower, respectively) than the average muscle pigment content of the population that the salmon belongs to.

The skilled person would be well aware of what such a normal population would be. However, for the avoidance of doubt, the population of salmon may be defined as a contemporary group of salmon, having been raised on the same feed and in the same environments (eg. in the same tanks and in the same net pens) throughout their lives. The population may be raised on commercially available, astaxhantin-containing, feed intended for farmed Atlantic salmon.

In practice, Atlantic salmon are usually or always farmed in large sea cages or water tanks, containing thousands of individuals (cohorts) of the same genetic origin and the same age, being fed the same feed ad libitum. Therefore, an individual animal should, and can easily be, compared with a random sample of its cohorts (for example, the random sample comprising at least 50 individuals), in order to determine whether its fillet colour is higher or lower than normal. Thus, an individual that has been selected (using the methods described here) to have a higher than normal ability to utilise pigment (eg astaxhantin) is expected to have a concentration of pigment which is higher than the mean pigment concentration within a random sample of its cohorts.

The presence or absence of the appropriate alleles of the DNA polymorphisms of the present invention can define whether the salmon has a greater or lesser than normal ability to utilise dietary pigment.

It should be noted that the method of predicting a salmon with a greater or lesser ability than normal to utilise dietary pigment, based on the determination of the alleles present at a DNA polymorphism, only applies if the DNA polymorphism in question is variable within the salmon population in question (ie if more than one allele of the DNA polymorphism is present within the population). One may determine whether or not a DNA polymorphism is variable within a population by genotyping at least 50 random animals from the population for the DNA polymorphism in question; the population may be defined to be variable if at least one copy of the rare allele (ie which ever of the alleles available is in the lowest number at the DNA polymorphism) is found within these 50 random animals.

The skilled person would be well aware of the target colour for consumers, but for the avoidance of doubt fillets that that possess the desired high intensity red colour may have a pigment content of at least 7 mg per kg of fillet and/or the equivalent of a Roche SalmoFan® score of 28 or more. Assuming the salmon are fed a normal dietary level of pigment (for example, 40-50 mg astaxhantin per kg of feed), salmon identified by the present invention to have a greater than normal ability to utilise pigment would likely present a pigment content of 7 mg per kg of fillet or more and/or the equivalent of a Roche SalmoFan® score of 28 or more. Salmon identified by the present invention to have a lesser than normal ability to utilise pigment would likely present a pigment content of less than 7 mg per kg of fillet and/or the equivalent of a Roche SalmoFan® score of less than 28.

The inventors have found that the DNA polymorphisms of the present invention can be present in either of two forms, i.e. the polymorphisms each have two alleles. One allele can be characterised as being associated with a salmon that has a greater than normal ability to utilise dietary pigment. Salmon that are homozygous for this allele would be expected to present fillets with a higher red colour intensity than normal (assuming the diet of that population includes pigment). Consequently, this allele is referred to hereinafter as the "red allele". The other allele can be characterised as being associated with salmon having less than normal abilities to utilise dietary pigment. Salmon that are homozygous for the other allele would be expected to present fillets with a lower red colour intensity than normal (assuming the diet of that population includes pigment). Consequently, this allele is referred to hereinafter as the "pale allele". A normal ability to utilise dietary pigment is defined as the mean ability (to utilise pigment) of the Atlantic salmon population in question. It is customary (part of the Art) and reasonable to assume that the ability to utilise dietary pigment correlates strongly with the pigment (e.g. astaxhantin) levels found in the muscle of individuals that have ingested pigment through the feed. Thus, estimates of pigment levels in muscle can be used as measures of the ability to utilise dietary pigment, and a normal ability to utilise dietary pigment translates to a normal pigment content in muscle. In any given population, the normal pigment level would be defined as the mean pigment level in a number of (for example, at least 50) random animals from the population.

Normal salmon are diploid organisms, and so possess two copies of the polymorphisms of the present invention (one copy to be found in each set of chromosomes). The step of determining the alleles in the method of the first aspect of the present invention therefore includes the step of analysing the form of DNA polymorphism provided in each set of chromosomes, i.e. determining whether each copy of the DNA polymorphism present is a red allele or is a pale allele. When a salmon subjected to the method of the present invention is determined to have two copies of the red allele for the DNA polymorphism (i.e. the salmon is homozygous for the red allele), the salmon is predicted to have a greater than normal ability to utilise pigment. Consequently, assuming such salmon are provided with pigment enriched diets, those fish would be expected to achieve a more intense red coloured fillet than normal fish fed on the same diet. Conversely, when a salmon subjected to the method of the present invention is determined to have two copies of the pale allele for the DNA polymorphism (i.e. is homozygous for the pale allele), the salmon is predicted to have a lesser than normal ability to utilise pigment. Consequently, assuming such salmon are provided with pigment enriched diets, those fish would be expected to achieve a lower intensity of red coloured fillet than normal fish fed on the same diet. When a salmon subjected to the method of the present invention is determined to have one copy of the red allele for the nucleotide polymorphism and one copy of the pale allele for that nucleotide polymorphism (i.e. is heterozygous), the salmon would be predicted according to the present invention to have a greater than normal ability to utilise pigment, if the red allele is less frequent in the population than the pale allele (possibly only a slightly greater ability). Consequently, assuming such salmon are provided with pigment enriched diets, those fish would be expected to achieve a more intense red coloured fillet than a population of normal fish fed on the same diet. Conversely, if the red allele is slightly more frequent in the population than the pale allele, a heterozygous animal would be predicted to have a lesser than normal ability to utilise pigment (possibly only slightly lower), and so would be expected to have a lower red colour intensity when compared to the average of the normal population of fish fed on the same diet.

The inventors have found that DNA polymorphisms that are associated with the ability for salmon to utilise dietary pigments are to be found in chromosomes 2, 14 and 26. Consequently, the one or more DNA polymorphism of the present invention may be provided in chromosome 2, 14 and/or 26 and that can predict the ability of a salmon to utilise dietary pigment (as described above). For example, the DNA polymorphisms of the present invention can be any of thirteen DNA polymorphisms found by the inventors to have this predictive ability and that are described below.

The DNA polymorphism may be any one or any combination of:

AGKD01307174.1_2657-AC (herein after referred to SNP No. 1),
AGKD01018473.1_11330-CT (herein after referred to SNP No. 2),
AGKD01018473.1_9476-AG (herein after referred to SNP No. 3),
AGKD01114288.1_6700-CT (herein after referred to SNP No. 4),
AGKD01407103.1_1854-AG (herein after referred to SNP No. 5),
  rs159406379 (herein after referred to SNP No. 6),
  rs159403576 (herein after referred to SNP No. 7),
  rs159407967 (herein after referred to SNP No. 8),
  rs159403150 (herein after referred to SNP No. 9),
AGKD01407103.1_3519-GT (herein after referred to SNP No. 10),
AGKD01087062.1_2136-CT (herein after referred to SNP No. 11),
AGKD01459927.1_723-AG (herein after referred to SNP No. 12), and
AGKD01004710.1_3497-AG (herein after referred to SNP No. 13).

Each of the DNA polymorphisms provided above are contemplated individually as part of the present invention. Methods of the present invention may therefore employ any one of the above DNA polymorphisms. Methods of the present invention may therefore employ any combination of the above DNA polymorphisms. For example, the DNA polymorphism of the present invention may be any one or any combination of SNPS 1, 2, 3, 4, 5, 6, 7, 8 and 9. For example, the DNA polymorphism of the present invention may be any one or any combination of SNP 1, 6 and 8. For example, the DNA polymorphism of the present invention may be any one or any combination of SNP 2, 6 and 8. For example, the DNA polymorphism of the present invention may be any one or any combination of SNP 1, 5 and 8. For example, the DNA polymorphism of the present invention may be any one or any combination of SNP 2, 5 and 8.

Eight of these DNA polymorphisms are located on chromosome 26 ie SNP Nos. 1, 2, 3, 4, 5, 7, 9 and 10.

The DNA polymorphism of the present invention may therefore be any one or any combination of SNPS 1, 2, 3, 4, 5, 7, 9 and 10.

For example, the DNA polymorphisms of the present invention may be either or both of SNPs 1 and 2.

Four of the DNA polymorphisms are located on chromosome 2, ie SNP Nos. 6, 11, 12, and 13.

The DNA polymorphism of the present invention may therefore be any one or any combination of SNP Nos. 6, 11, 12, and 13.

The DNA polymorphism of the present invention may be rs159407967, ie SNP 8 (located on chromosome 14).

Furthermore, SNPS 1, 2, 3, 4, 5, 7, 9, and 10 are located within a narrow region (covering 5.7 million base pairs of a genome that is approximately 3.0 billion base pairs long; i.e. 0.018% of the genome) on chromosome 26 (Tables 3 and 4). It is therefore highly reasonable to assume that these seven DNA polymorphisms co-segregate with one and the same causative mutation. In other words, these seven DNA polymorphisms function as (DNA) markers of one and the same QTL. Therefore, these seven DNA polymorphisms comprise one unit, and in practice one could use only one of these DNA polymorphisms in a method of predicting a salmon's ability to utilise dietary pigment. Consequently, each of the DNA polymorphisms provided above are contemplated individually as part of the present invention.

Similarly, SNPs 6, 12, 13, and 14 are located within one and the same narrow region on chromosome 2. It is therefore likely that these SNPs co-segregate with one and the same causative mutation. Therefore, these four DNA polymorphisms comprise one unit, and in practice one could use only one of these DNA polymorphisms in a method of predicting a salmon's ability to utilise dietary pigment. Consequently, each of the DNA polymorphisms provided above are contemplated individually as part of the present invention.

For most polymorphic loci (in any species), there will be a number of other loci having identical or highly similar genotype patterns. To illustrate, two loci have identical or nearly identical genotype patterns if all or most animals having genotype AA at locus 1 have genotype CC at locus 2, all or most animals having genotype AB at locus 1 have genotype CD at locus 2, and all or most animals having genotype BB at locus 1 have genotype DD at locus 2. In genetic terms, two such loci will be said to be in linkage disequilibrium (LD) with each other. The DNA polymorphisms of the present invention as specified above may therefore be replaced by other DNA polymorphisms with which they are in LD. Consequently, the present invention may therefore relate to a method where one or more of the polymorphisms (described above) are replaced by other loci with which they are in sufficiently strong LD. Here, sufficiently strong LD is defined as follows: Two loci are in sufficiently strong LD with each other if the square of the correlation coefficient between the two loci ($r^2$; a common measure of LD) is greater than 0.3. This number (0.3) is commonly regarded as the lower threshold for defining 'sufficiently strong LD' (see e.g. Uimari et al. 2005).

The method may employ two or more of the polymorphisms of the present invention, for example three polymorphisms. For example the methods of the present invention may involve the step of determination on the basis of one DNA polymorphism from chromosome 26 (eg SNP 1 or 2), one DNA polymorphism from chromosome 2 (eg SNP 6 or 11), and the DNA polymorphism from chromosome 14 (SNP 8). For example, the methods of the present invention may involve the step of determination on the basis of any one DNA polymorphism selected from the group consisting of SNPs 1, 2, 3, 4, 5, 7 9 and 10, and any one DNA polymorphism selected from the group consisting of SNPs 6, 12, 13 and 14, optionally additional with SNP 8. When two or three polymorphisms are used, the salmon having the red allele at all two/three polymorphisms are expected to have the highest ability to utilise dietary pigment, and so the highest intensity red fillet colour. More precisely, the invention would be most effective if the polymorphisms used in the method comprised or consisted SNP1 (AGKD01307174.1_2657-AC; chromosome 26) in combination with SNP 6 (rs159406379; chromosome 2) and SNP 8 (rs159407967; chromosome 14). Alternatively, SNP2 (AGKD01018473.1_11330-CT) could replace SNP1 (AGKD01307174.1_2657-AC) as the representative of chromosome 26, and/or SNP 11 (AGKD01087062.1_2136-CT) could replace SNP 6 (rs159406379) as the representative of chromosome 2.

The identity of that base which defines the red or pale allele for each polymorphism for use in the methods of the present invention is provided in Table 2. The identities of the red- and pale alleles provided in Table 2 are relative to the DNA sequences provided in Table 5 (note: a DNA strand can be read in two directions, for example, the DNA sequence ACAGT would become CATGT if read in the other (so-called reverse-complement) direction, and the middle base would be nominated as A or T, respectively, in these two cases). For example, when the methods of the present invention include the determination of the allele present at SNP1, if the allele is determined to be A at the variant position of SNP1 (defined by square bracket in Table 5), and provided that the DNA strand is read in the read direction used in Table 5, then the allele is determined to be a red allele. If the allele is determined to be C at the variant position of SNP1 (provided that the DNA strand is read in the read direction used in Table 5), then the allele is determined to be the pale allele.

The associated sequence listing provides a sequence for each allele for each of the above described polymorphisms. SEQ ID Nos 1 through 13 correspond to red alleles for SNPs 1 through 13, respectively. SEQ ID Nos 14 through 26 correspond to the pale alleles for SNPs 1 through 13, respectively. For example, when a salmon is determined to have two copies of SEQ ID NO. 1 at the SNP corresponding to SNP 1 (i.e. two copies of the adenosine (A) allele at that SNP), then that salmon is homozygous for the allele that confers a greater than normal ability to utilise dietary pigment. Consequently, that salmon is predicted, according to the present invention, to have a greater than normal ability to utilise dietary pigment. Conversely, when the salmon is determined to have two copies of SEQ ID NO. 14 at the SNP corresponding to SNP 1 (i.e. two copies of the cytosine (C) allele at that SNP), then that salmon is homozygous for the allele that confers a lower than normal ability to utilise dietary pigment. Consequently, that salmon is predicted, according to the present invention, to have a lower than normal ability to utilise dietary pigment.

Most of the DNA polymorphisms described throughout this application are defined with reference to the first version of the whole genome sequence for *Salmo solar* published in GenBank under accession number AGKD00000000 (version AGKD00000000.1 GI: 354459050). More particularly, most DNA polymorphisms in the present application have been given names that reflect the contig (subsequence) of AGKD00000000.1 within which the DNA polymorphism in question reside, the position of the DNA polymorphism within the contig, and the alleles present at the DNA polymorphism. More specifically, the DNA polymorphisms have been given names following the scheme:

<GenBank accession number of contig>_<position of DNA polymorphism within contig>-<alleles found at the DNA polymorphism>, where the identity of the alleles is dictated by the read direction used in Table 5. Some SNPs (those that are to be found in dbSNP) are named according to their dbSNP rs number.

For example, the DNA polymorphism may be AGKD01307174.1_2657-AC. This polymorphism is located at position 2657 within contig AGKD01307174.1 (which is part of reference sequence AGKD00000000.1), and the alleles that can be found are A and C. Alternatively, the DNA polymorphism may be rs159406379, being a single nucleotide polymorphism (SNP) found within the dbSNP database, hosted by the *National Center for Biotechnology Information* (NCBI; USA), i.e. (http://www.ncbi.nlm.nih.gov/projects/SNP/).

Each of the above nucleotide polymorphisms are contemplated individually as part of the present invention.

The method may be applied to Atlantic salmon (i.e. *Salmo solar*).

The step of determining which alleles are present in a salmon and at a specific DNA polymorphism may be practised on a sample taken from the salmon. The sample may be any sample in which analysis of nucleic acid material is possible, as would be readily understood by the person skilled in the art. For the avoidance of doubt, the sample may be a muscle tissue sample, blood sample, liver sample and/or a fin clip.

The skilled person would be well aware of all available methods capable of determining the genotypes (i.e. combination of alleles) that an animal has at a DNA polymorphism. For example, the method may involve sequence analysis of the salmon to be tested. Alternatively, the method may involve single base extension of DNA fragments terminating at the polymorphic site (e.g. iPLEX assays from Sequenom and Infinium assays from Illumina), allele-specific PCR (e.g. SNPtype assays from Fluidigm or KASPar assays from KBiosciences), or competitive hybridisation of probes complementary to the different alleles (e.g. the TaqMan assay from Applied Biosystems).

Consequently, in a further aspect of the present invention, there is provided a hybridisation probe that is specific for one or more of the aforementioned DNA nucleotide polymorphisms.

A salmon that is predicted to have greater than normal ability to utilise dietary pigment according to the first aspect of the present invention is more likely than normal to produce offspring that have greater than normal ability to utilise dietary pigment (and so ability to provide fillets with the desired high intensity red colour). Consequently, in a further aspect of the present inventions, there is provided a method of selecting a salmon for use as broodstock, wherein the salmon is selected based on the prediction by the method as claimed in the first aspect of the present invention that the salmon will provide a greater than normal ability to utilise dietary pigment.

Conversely, a salmon predicted by the method of the first aspect of the present invention as not providing a greater than normal utilisation of dietary pigment would not be selected as broodstock.

Also contemplated as forming part of the present invention is an isolated polynucleotide comprising one or more of the single nucleotide polymorphisms selected from the group provided in Table 5 located within a portion of the salmon genome.

Dietary carotenoids, such as astaxanthin and canthaxanthin, are Vitamin A precursors. Vitamin A precursors are mainly metabolised in the intestine or liver, where they are cleaved by oxygenases into retenoids or apo-carotenals. Excess carotenoids that have not been cleaved are incorporated into lipoproteins and secreted into the bloodstream, from where they are taken up by muscle cells and deposited, binding to actomyosin. One key enzyme in the catabolism of Vitamin A precursors is Beta-Carotene 15,15'-Monooxygenase 1 (Bcmo1; coded by gene bcmo1), performing oxidative cleavage of beta-carotene. The two SNPs most strongly associated with fillet colour, AGKD01307174.1_2657-AC (SNP 1) and AGKD01018473.1_11330-CT (SNP 2) (both being part of this application), are both located within or near the 3'-untranslated region of a gene encoding a protein similar to Bcmo1. This gene, and its corresponding protein product, will be referred to, respectively, as bcmo1-like and Bcmo1-like from here on. Concentrations of both circulatory- and muscle-bound carotene, as well as flesh coloration, have been shown to be affected by genetic variation in regulatory elements of bcmo1 in mammalian and avian species (Ferruci et al. 2009, Lietz et al. 2012, Hendrickson et al. 2012, Le Bihan-Duval et al. 2011, Jlali et al. 2012). The applicants have determined experimentally that the protein product of the bcmo1-like gene located on chromosome 26 is capable of cleaving beta-carotene in vivo. The surprising co-localisation of bcmo1-like and SNPs strongly associated with fillet colour in Atlantic salmon strongly indicate that bcmo1-like is a key regulator of fillet colour in Atlantic salmon. In other words, within the copy of bcmo1-like located on Atlantic salmon chromosome 26, or within the sequence regions flanking that gene, one or more polymorphisms reside which modify the activity of the Bcmo1-like protein product, thereby changing the levels of muscle-bound astaxanthin/canthaxanthin. This/these polymorphism(s) may be identical to AGKD01307174.1_2657-AC and/or AGKD01018473.1_11330-CT, or they may be other, yet undiscovered, polymorphisms within or in the vicinity of bcmo1-like or bcmo1

Furthermore, given that bcmo1-like and/or bcmo1 are partly responsible for determining how good a salmon is at utilising dietary pigment, one route towards increasing a salmon's ability to utilise dietary pigment would be to modify the concentrations or the activities of the protein products corresponding to these genes. More specifically, one could use antisense mRNA in order to inhibit the translation of the bcmo1-like and/or bcmo1 mRNA, given that antisense mRNA could be delivered to the relevant cells. Alternatively, one could administer inhibitors of the Bcmo1-like and/or Bcmo1 protein products to the animals.

In a further aspect of the present invention there is provided a method of improving the ability of a salmon to utilise dietary pigment, the method including the step of administering an agent that inhibits the expression of the genes bcmo1-like and/or bcmo1 and/or an agent that inhibits the activity of the proteins Bcmo1-like and/or Bcmo1 (the activity may be the enzymatic digestion by Bcmo1-like and Bcmo1). The agent may, for example, be anti-sense mRNA that inhibits the translation of bcmo1-like and/or bcmo1 mRNA.

BRIEF DESCRIPTION OF DRAWINGS

The present invention will now be described by way of example with reference to the accompanying figures, in which.

DETAILED DESCRIPTION

Figure 1:
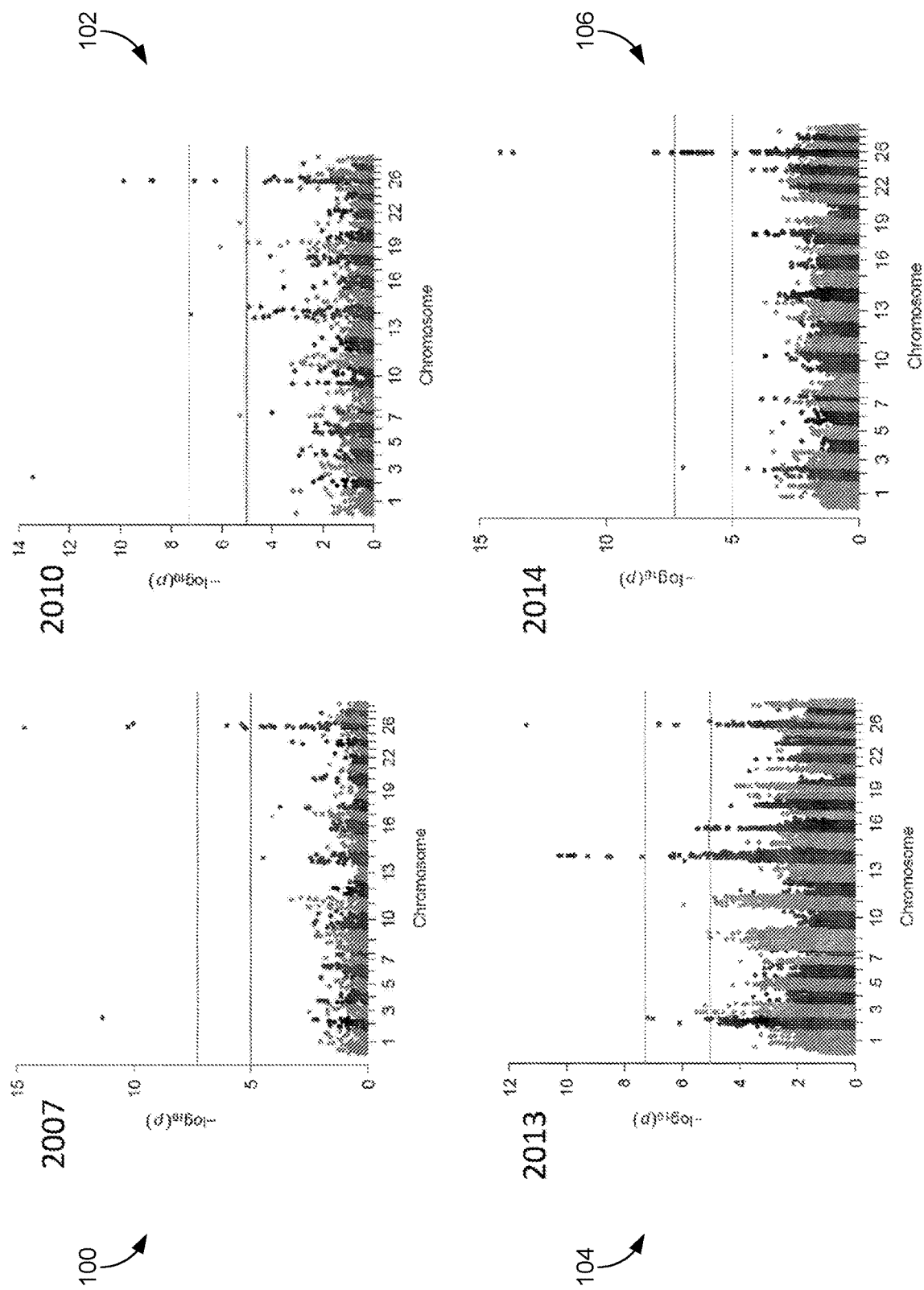
FIG. 1 displays Manhattan plots from GWAS experiments conducted on Sample sets 1 through 4, corresponding to experiments conducted in 2007, 2010, 2013, and 2014. Each dot of the plot corresponds to one SNP, the x-coordinate of the dot corresponding to the physical position of the SNP within the Atlantic salmon genome and the y-coordinate corresponding to the negative of the 10-based logarithm of the p-value of the test for association between fillet colour and genotypes at the SNP. The upper horizontal line corresponds to the threshold for experiment-wise significance (assuming H0 (null hypothesis; to be refuted)=none of the tested SNPs have an effect upon fillet colour, and H1 (alternative hypothesis): the SNP in question has an effect on fillet colour), and the lower horizontal line corresponds to a more lenient, "suggestive" level of significance.

1. Fillet Colour Analysis of Test Animals

Fillet colour was analysed for salmon fillets taken from 6701 Atlantic salmon belonging to the AquaGen breeding population. This breeding population was formed in the early 1970s, on the basis of Atlantic salmon sampled from different Norwegian rivers.

Fillet colour was analysed in three independent test rounds, taking place in 2007, 2010, and 2013, respectively. In all three rounds, fillet colour was measured on the flesh side of fresh salmon fillets. In 2007 and in 2013, fillet colour was measured using a QVision Analyser, a spectrophotometer which measures absorption/reflection at 400-1200 nm wavelengths. In 2010, fillet colour was measured using the Photofish method, a method which is based on image analysis of photographs taken under standardised conditions (i.e. inside a closed box with constant light). Irrespective of method, the fillet colour measurements were converted to units of mg astaxhantin per kg of fillet. In each of the three test years, the conversions were based on the correlation between HPLC measurements and QVision/Photofish measurements in a sample of 50 salmon that had been analysed by High-Performance Liquid Chromatography (HCPL) as well as by the QVision analyser or using Photofish.

Within each of the three test rounds (2007, 2010, 2013), all fillet colour measurements were done under identical conditions.

In each test round, tissue samples (from skeletal muscle, liver, or heart) were taken from a subset of the animals whose fillet colour had been measured. DNA was extracted from these tissues using a standard method (using the DNAeasy 96 kit from QIAGEN, following the protocol supplied by QIAGEN). These DNA samples were later used for genotyping. In each test round, the selection of animals for DNA-extraction and genotyping was based on sets of criteria that were unrelated to the animals' fillet colour measurements or to the expected performance of the animal with regard to fillet colour.

From here on, the sample sets corresponding to the 2007, 2010, and 2013 test rounds will be referred to as Sample Set 1, Sample Set 2, and Sample Set 3. Sample Sets 1, 2, and 3 were derived from consecutive generations of the AquaGen breeding nucleus. Table 1 displays the numbers of individuals, full-sib groups, fathers, and mothers pertaining to each sample set. Data sets 1, 2, and 3 are the data sets corresponding to sample sets 1, 2, and 3; the date sets encompassing genotype data and phenotype data.

TABLE 1

Sample/data sets

| Data set | Year | Genotyping technol. | N animals | N FS groups | N fathers | N mothers | N markers | Mean weight (gram) |
|---|---|---|---|---|---|---|---|---|
| 1 | 2007 | Illumina + Sequenom | 2891 | 265 | 177 | 141 | 5650 + 96* | 2845 |
| 2 | 2010 | Illumina 6k | 1847 | 308 | 241 | 242 | 4423 | 3024 |
| 3 | 2013 | Affymetrix 220k | 1963 | 99 | 68 | 69 | 219,998 | 3853 |

Year = year of sampling and phenotypic measuring;
Genotyping technol. = technology used for genotyping the data set (see more detailed description below);
N animals = number of animals having been genotyped and phenotyped ('offspring');
N FS groups = number of full-sibling groups represented by genotyped and phenotyped animals;
N fathers and N mothers = number of fathers and mothers of the phenotyped and genotyped animals;
N markers = number of DNA polymorphisms genotyped.
*96 additional DNA polymorphisms were identified by de novo SNP-detection within a particular genomic region (the region containing the genes bcmo1 and bcmo1-like), these DNA polymorphisms were genotyped using Sequenom techology, whereas the other 5650 DNA polymorphisms were genotyped using Illumina technology.

2. Genotyping of Test Animals

Sample Set 1 was genotyped using a customdesigned iSelect SNP-array from Illumina (San Diego, Calif., USA), containing approximately 6,000 working SNP-assays developed in-house at CIGENE. Of these 6,000 SNPs, 5650 were polymorphic within sample set 1. Sample Set 2 was genotyped using another customdesigned iSelect SNP-array from Illumina, this array being a slightly modified form of the array used on Sample Set 1. Of the approximately 6,000 working SNPs on this array, 4423 were polymorphic within Sample Set 2. The number of SNPs common to the two sets was 4308.

The SNP-arrays used for genotyping Sample Set 1 and Sample Set 2 contained SNPs that were mostly derived from the alignment of publicly available EST sequences or from sequencing of genome complexity reduction (GCI) libraries using 454 technology (Lien et al. 2011). The samples were genotyped following standard protocols for iSelect SNP-arrays, provided by Illumina. Bead-arrays were scanned on an iScan reader using a modified Infinium II scan settings protocol which records bead-level intensity data in .txt format.

Sample Set 3 was genotyped using a custom Axiom array from Affymetrix (San Diego, Calif., USA). The SNPs on this array were identified through whole genome sequencing of 29 Atlantic salmon from the AquaGen breeding nucleus in addition to three double haploid (androgenetically derived) Atlantic salmon. The SNP array contained 200,000 SNPs that were polymorphic within Sample Set 3. Genotyping was done according to the Axiom 2.0 Assay Manual Workflow User Guide (http://media.affymetrix.com/support/downloads/manuals/axiom_2_assay_manua l_workflow_prepguide.pdf). Genotype calling was done using the Affymetrix Power Tools programs (http://www.affymetrix.com/estore/partners_programs/programs/developer/tool s/powertools.affx), according to "best practices" recommendations from Affymetrix (http://media.affymetrix.com/support/downloads/manuals/axiom_best_practice_s upplemen-t_user_guide.pdf).

Sample Set 1 was, in addition to being genotyped with the above-mentioned Illumina iSelect SNP-array, also genotyped for a further set of 96 SNPs*. These 96 SNPs were identified by targeted-SNP detection on a genomic scaffold containing the candidate gene in question (this gene being bcmo1-like). The genomic scaffold had been developed by de novo assembly of reads coming from the International Collaboration to Sequence the Atlantic Salmon Genome (ICSASG: Davidsson et al). The reads that were aligned to the reference sequence (in order to identify SNP and other polymorphisms) were obtained through sequencing 45 and 29 AquaGen-animals to 2× and 15× genome coverage, respectively, on Illumina HiSeq2000. The reads were aligned using bowtie2, and SNPs were detected using freebayes. The novel SNPs were genotyped in sample set 1, using the MassArray iPLEX platform from Sequenom (San Diego, USA), following the standard iPLEX protocol provided by Sequenom.

3. Testing for Association Between SNP Alleles and Fillet Colour

In order to identify QTL for fillet colour, data sets 1, 2, and 3 were analysed with a linear mixed model solved using the software DMU, each SNP being analysed individually. In other words, a genome-wide association study (GWAS) for fillet colour was performed. The dependent variable was the astaxanthin content in muscle, derived as described above. The linear mixed model was an animal model containing the fixed effect of the animal's sex, the fixed regression on the animal's round weight (weight before slaughter), and the random regression on the number of copies of allele A carried by the animal (allele A being one of the two alleles present at the SNP).

Some DNA polymorphisms were shared by all three datasets, while others were shared by two datasets or by none. More specifically, 2,724 DNA polymorphisms were shared by all three datasets, while 1,771 DNA polymorphisms were shared by only two datasets. We applied the following criteria for declaring a DNA polymorphism as predictive of fillet colour: 1) the DNA polymorphism must be shared by at least two datasets, 2) the DNA polymorphisms p-value must be smaller than 0.001 in all individual datasets, 3) the overall p-value must be smaller than $10^{-17}$. The overall p-value was derived from the sum of the individual likelihood ratio test (LRT) statistics, the sum of the LRT statistics being $\chi^2$-distributed with degrees of freedom equal to the number of tests (ie 2 or 3). The threshold for overall p-value ($10^{-17}$) corresponded to the threshold for DNA polymorphisms that were informative in all three data sets, when a significance threshold of $\alpha=0.05$ and a Bonferroni correction for multiple testing in each of the three data sets was applied. Given that the individual tests performed within each data sets were not independent of each other, this overall significance threshold was very strict. Nine SNPs were found to fulfill these criteria (SNP 1 through 9 of Table 2). Using nucleotide BLAST, the Atlantic salmon genome scaffolds (from build 2 of the Atlantic salmon genome sequence) harbouring these SNPs were identified. The chromosomes harbouring the SNPs were identified by two-point linkage analysis using Data Set 3. Later, when build 4 of the Atlantic salmon genome sequence became available, nucleotide BLAST against build 4 was performed in order to position the SNPs relative to this sequence (Table 3). Chromosome sequences (contiguous DNA sequences correspond to whole Atlantic salmon chromosomes), submitted to GenBank but not yet released by GenBank, were provided by Sigbjørn Lien (one of the inventors and a partner in the ICSASG), and used in order to confirm the genome positions of the SNPs (Table 4). The chromosomes that the SNPs belong to are also evident from inspection of the GenBank records of the scaffolds that the SNPs map to (listed in Table 3). For example, SNP1 (AGKD01307174.1_2657-AC) map to the genome scaffold having GenBank identifier AGKD04000059. According to the GenBank record, the additional identifier of this scaffold is tcf1000000010_0-0_ssa26_0_0, reflecting that the SNP is located on chromosome 26. Consequently, reference to the polymorphisms of the present invention, and alleles of these polymorphism, as discussed earlier in the present application correspond to and so are seen to include definition of the polymorphisms and alleles defined with reference to their position within the Atlantic salmon genome as provided in table 3.

Following the three initial GWAS experiments, a fourth experiment was carried out in order to further confirm the results. See FIG. 2. In this experiment, a number of SNPs were tested that had not been tested earlier. Some of these, all of them located on chromosomes 2 or 26, were found to be strongly associated with fillet colour (SNPs 10 through 13 of Table 2). Details on the fourth experiment can be found below.

The LRT statistics of the SNPs strongly associated with fillet colour can be found in Table 2. As can be seen from Table 3, eight of the thirteen SNPs reside within one and the same genome scaffold. It is reasonable to assume that these SNPs tag one and the same QTL, this QTL being located on chromosome 26 (Tables 3 and 4). The other two SNPs are located on chromosomes 2 and 14, respectively (Tables 3 and 4). The flanking sequences of the SNPs can be found in Table 5. Four of the SNPs are denoted by their dbSNP rs # identifiers (http://www.ncbi.nlm.nih.gov/projects/SNP/). The remaining have been given names according to this scheme: <build1-contig>_<position of SNP in build1-contig>-<SNP alleles>, where build1-contig is the contig, from the Atlantic salmon genome sequence build 1 (GenBank identifier AGKD00000000.1), to which the SNP maps, and SNP-alleles are the alleles found at the SNP (when the DNA is "read" in the direction dictated by Table 5). The SNPs that did not have dbSNP rs # identifiers were submitted to dbSNP by the inventors, and have been provided with dbSNP ss # identifiers (Table 6).

TABLE 2

Likelihood Ratio Test (LRT) statistics on the thirteen significant SNPs.

| SNP # | SNP | Inform. data sets | overall LRT | Red all. | Pale all. |
|---|---|---|---|---|---|
| 1 | AGKD01307174.1_2657-AC | 1, 3 | 296.1 | A | C |
| 2 | AGKD01018473.1_11330-CT | 1, 3 | 296.1 | T | C |
| 3 | AGKD01018473.1_9476-AG | 1, 3 | 172 | G | A |
| 4 | AGKD01114288.1_6700-CT | 1, 3 | 159.3 | C | T |
| 5 | AGKD01407103.1_1854-AG | 1, 3 | 133.7 | A | G |
| 6 | rs159406379 | 1, 2 | 105.2 | G | T |
| 7 | rs159403576 | 1, 2, 3 | 108.2 | C | A |
| 8 | rs159407967 | 1, 2, 3 | 89.2 | G | A |
| 9 | rs159403150 | 1, 2 | 84 | T | C |
| 10 | AGKD01407103.1_3519-GT | 4 | 33.4 | G | T |
| 11 | AGKD01087062.1_2136-CT | 4 | 28.1 | C | T |
| 12 | AGKD01459927.1_723-AG | 4 | 16.8 | G | A |
| 13 | AGKD01004710.1_3497-AG | 4 | 13.9 | G | A |

Inform. data sets = data sets that included the SNP in question;
overall LRT = the sum of likelihood ratio statistic (summarised across informative data sets);
Red all. = red allele;
Pale all. = pale allele.

TABLE 3

Position of the 13 significant SNPs, relative to build 4 of the Atlantic salmon genome assembly (GenBank identifier of assembly: AGKD00000000.4), and reference allele of each SNP within that assembly.

| SNP # | SNP | Position within scaffold | GenBank identifier of scaffold | Reference allele |
|---|---|---|---|---|
| 1 | AGKD01307174.1_2657-AC | 424633 | AGKD04000059 | A |
| 2 | AGKD01018473.1_11330-CT | 427079 | AGKD04000059 | T |

TABLE 3-continued

Position of the 13 significant SNPs, relative to build 4 of the Atlantic salmon genome assembly (GenBank identifier of assembly: AGKD00000000.4), and reference allele of each SNP within that assembly.

| SNP # | SNP | Posistion within scaffold | GenBank identifier of scaffold | Reference allele |
|---|---|---|---|---|
| 3 | AGKD01018473.1_9476-AG | 428933 | AGKD04000059 | G |
| 4 | AGKD01114288.1_6700-CT | 426289 | AGKD04000059 | C |
| 5 | AGKD01407103.1_1854-AG | 454198 | AGKD04000059 | G |
| 6 | rs159406379 | 96516 | AGKD04002098 | T |
| 7 | rs159403576 | 6077666 | AGKD04000059 | C |
| 8 | rs159407967 | 1557767 | AGKD04000304 | G |
| 9 | rs159403150 | 3304224 | AGKD04000059 | C |
| 10 | AGKD01407103.1_3519-GT | 455863 | AGKD04000059 | T |
| 11 | AGKD01087062.1_2136-CT | 26332 | AGKD04002098 | C |
| 12 | AGKD01459927.1_723-AG | 9571 | AGKD04004383 | G |
| 13 | AGKD01004710.1_3497-AG | 16637 | AGKD04004092 | A |

TABLE 4

Chromosomes, and positions within chromosomes, of the 13 significant SNPs

| SNP # | SNP | Chromosome* | Position within chromosome |
|---|---|---|---|
| 1 | AGKD01307174.1_2657-AC | ssa26 | 19081573 |
| 2 | AGKD01018473.1_11330-CT | ssa26 | 19079127 |
| 3 | AGKD01018473.1_9476-AG | Ssa26** | not determined** |
| 4 | AGKD01114288.1_6700-CT | ssa26 | 19079917 |
| 5 | AGKD01407103.1_1854-AG | ssa26 | 19052008 |
| 6 | rs159406379 | ssa02 | 71437050 |
| 7 | rs159403576 | Ssa26** | not determined** |
| 8 | rs159407967 | ssa14 | 38860943 |
| 9 | rs159403150 | ssa26 | 16201976 |
| 10 | AGKD01407103.1_3519-GT | ssa26 | 19050343 |
| 11 | AGKD01087062.1_2136-CT | ssa02 | 71366866 |
| 12 | AGKD01459927.1_723-AG | ssa02 | 69273037 |
| 13 | AGKD01004710.1_3497-AG | ssa02 | 56685383 |

*The chromosome sequences pertain to Atlantic salmon genome build 4. Each chromosome sequence is an amalgam of scaffolds from Atlantic salmon genome build 4 (such as the scaffolds listed in Table 3), the scaffolds having been sorted and oriented using genetic linkage analysis and other appropriate techniques. The chromosome sequences have been submitted to GenBank by one of the inventors (Dr. Sigbjørn Lien), and are due to be made public by GenBank in 2015.

For reasons connected to the synthesis of chromosome sequences from Atlantic salmon genome build 4.0 scaffolds, two SNP sequences did not match the available chromosome sequences. However, both SNPs can be deduced to be located on chromosome 26 due to the fact that they map to scaffolds that were found to map to chromosome 26 (compare Table 3 and Table 4).

TABLE 5

Sequences of the 13 significant SNPs

| SNP | SEQ ID NO: | Sequence |
|---|---|---|
| AGKD01307174.1_2657-AC (SNP 1) | SEQ ID NO: 1 | TTGCCCTCTACAATGTTAAGGTACAATCCTGCCCTATGCTGGTTATGTCAGTTGGTGCTCTGTGTGGGAA |
|  | SEQ ID NO: 14 | TTGCCCTCTACAATGTTAAGGTACAATCCTGCCCTCTGCTGGTTATGTCAGTTGGTGCTCTGTGTGGGAA |
| AGKD01018473.1_11330-CT (SNP2) | SEQ ID NO: 2 | AGATGATCACTGCAAAATGTTCAAGTTTTATATCATATTTTGCTATTTACATTTACTGTGCATGAGAAGCCA |
|  | SEQ ID NO: 15 | AGATGATCACTGCAAAATGTTCAAGTTTTATATCACATTTTGCTATTTACATTTACTGTGCATGAGAAGCCA |
| AGKD01018473.1_9476-AG (SNP 3) | SEQ ID NO: 3 | TTCTTATCAAAACAAAAATAAGTCTGGTTGGAGGAGCATTTCTTTGTGGGTTTTTTGGGAGGTCATTGAG |

TABLE 5-continued

Sequences of the 13 significant SNPs

| SNP | SEQ ID NO: | Sequence |
|---|---|---|
| | SEQ ID NO: 16 | TTCTTATCAAAACAAAAATAAGTCTGGTTGGAGGAACATT TCTTTGTGGGTTTTTTGGGAGGTCATTGAG |
| AGKD01114288.1_6 700-CT (SNP 4) | SEQ ID NO: 4 | TTTCCCATGGGAGAAGGGGAGCAACACTAACAATCATAC CAACTGATCTTAACGTTTTTCTAGTTTTTC |
| | SEQ ID NO: 17 | TTTCCCATGGGAGAAGGGGAGCAACACTAACAATTATAC CAACTGATCTTAACGTTTTTCTAGTTTTTC |
| AGKD01407103.1_1 854-AG (SNP 5) | SEQ ID NO: 5 | GCTTTCATATATTTAAGATTTGAGGACCATGTAAAACAAT CTCACCATCATCCTCTCCTTCTCCATTGGG |
| | SEQ ID NO: 18 | GCTTTCATATATTTAAGATTTGAGGACCATGTAAAGCAAT CTCACCATCATCCTCTCCTTCTCCATTGGG |
| rs159406379 (SNP 6) | SEQ ID NO: 6 | ACACGCGACAGCCCCGTCACTCCGCAGCTGGGTCGGAACC GTAGGAACGGTCTCCACGACGTCGACCTGA |
| | SEQ ID NO: 19 | ACACGCGACAGCCCCGTCACTCCGCAGCTGGGTCGTAACC GTAGGAACGGTCTCCACGACGTCGACCTGA |
| rs159403576 (SNP 7) | SEQ ID NO: 7 | ATTCCATTTGCTACTGACAGCTTTCTTGGTTGCCAAGGTG ATGAATCCTATACCTATACCATATC |
| | SEQ ID NO: 20 | ATTCCATTTGCTACTGACAGCTTTCTTGGTTGACAAGGTG ATGAATCCTATACCTATACCATATC |
| rs159407967 (SNP 8) | SEQ ID NO: 8 | GTAAAACAATCAATCATTTATCTGTGCTTTTACTCGTCCA GTTTGATGCCAATGCAGTTGGAGGAAAGGA |
| | SEQ ID NO: 21 | GTAAAACAATCAATCATTTATCTGTGCTTTTACTCATCCA GTTTGATGCCAATGCAGTTGGAGGAAAGGA |
| rs159403150 (SNP 9) | SEQ ID NO: 9 | TGGATACTGAGTCACGGTTTTAAAAGCCTNTCATGTGCTC TCTCCGTTTGCAGAGCACTTGTGATGGTCT |
| | SEQ ID NO: 22 | TGGATACTGAGTCACGGTTTTAAAAGCCTNTCATGCGCTC TCTCCGTTTGCAGAGCACTTGTGATGGTCT |
| AGKD01407103.1_3 519-GT (SNP10) | SEQ ID NO: 10 | ATGCAGTTTGGGCTGGGTTTTTGGTTGTTTTTCCAGTTAG TATTTTCTTGAACTTATGAGTGCATCTATGC |
| | SEQ ID NO: 23 | ATGCAGTTTGGGCTGGGTTTTTGGTTGTTTTTCCATTTAG TATTTTCTTGAACTTATGAGTGCATCTATGC |
| AGKD01087062.1_2 136-CT (SNP11) | SEQ ID NO: 11 | TTGTCCTCATTCCAGGACAGCTGTTGATTCACCAACCTTT TCTCCATTTAGTCCGCACTACCGGCCGCCA |
| | SEQ ID NO: 24 | TTGTCCTCATTCCAGGACAGCTGTTGATTCACCAATCTTT TCTCCATTTAGTCCGCACTACCGGCCGCCA |
| AGKD01459927.1_7 23-AG (SNP12) | SEQ ID NO: 12 | GTATTGGATTCATTAGGGCTGGGTGTCTGTGATGCGTTGT TTTGATTCCCCACTTGTCTTCTGGACAAA |
| | SEQ ID NO: 25 | GTATTGGATTCATTAGGGCTGGGTGTCTGTGATGCATTGT TTTGATTCCCCACTTGTCTTCTGGACAAA |
| AGKD01004710.1_3 497-AG (SNP13) | SEQ ID NO: 13 | AAGACAAGTAGTAGTCTTTACTAGATTATGTTTAAGTCA ACAAAATGTGTCTTACATTTACAAAAAGCCT |
| | SEQ ID NO: 26 | AAGACAAGTAGTAGTCTTTACTAGATTATGTTTAAATCA ACAAAATGTGTCTTACATTTACAAAAAGCCT |

TABLE 6 dbSNP identifiers of SNPs submitted to dbSNP by the authors.

| SNP # | SNP | dbSNP identifier |
|---|---|---|
| 1 | AGKD01307174.1_2657-AC | ss1751859087 |
| 2 | AGKD01018473.1_11330-CT | ss1751859088 |
| 3 | AGKD01018473.1_9476-AG | ss1751859089 |
| 4 | AGKD01114288.1_6700-CT | ss1751859090 |

TABLE 6-continued dbSNP identifiers of SNPs submitted to dbSNP by the authors.

| SNP # | SNP | dbSNP identifier |
|---|---|---|
| 5 | AGKD01407103.1_1854-AG | ss1751859091 |
| 10 | AGKD01407103.1_3519-GT | ss1751859093 |
| 11 | AGKD01087062.1_2136-CT | ss1751859094 |
| 12 | AGKD01459927.1_723-AG | ss1751859095 |
| 13 | AGKD01004710.1_3497-AG | ss1751859096 |

Figure 2:
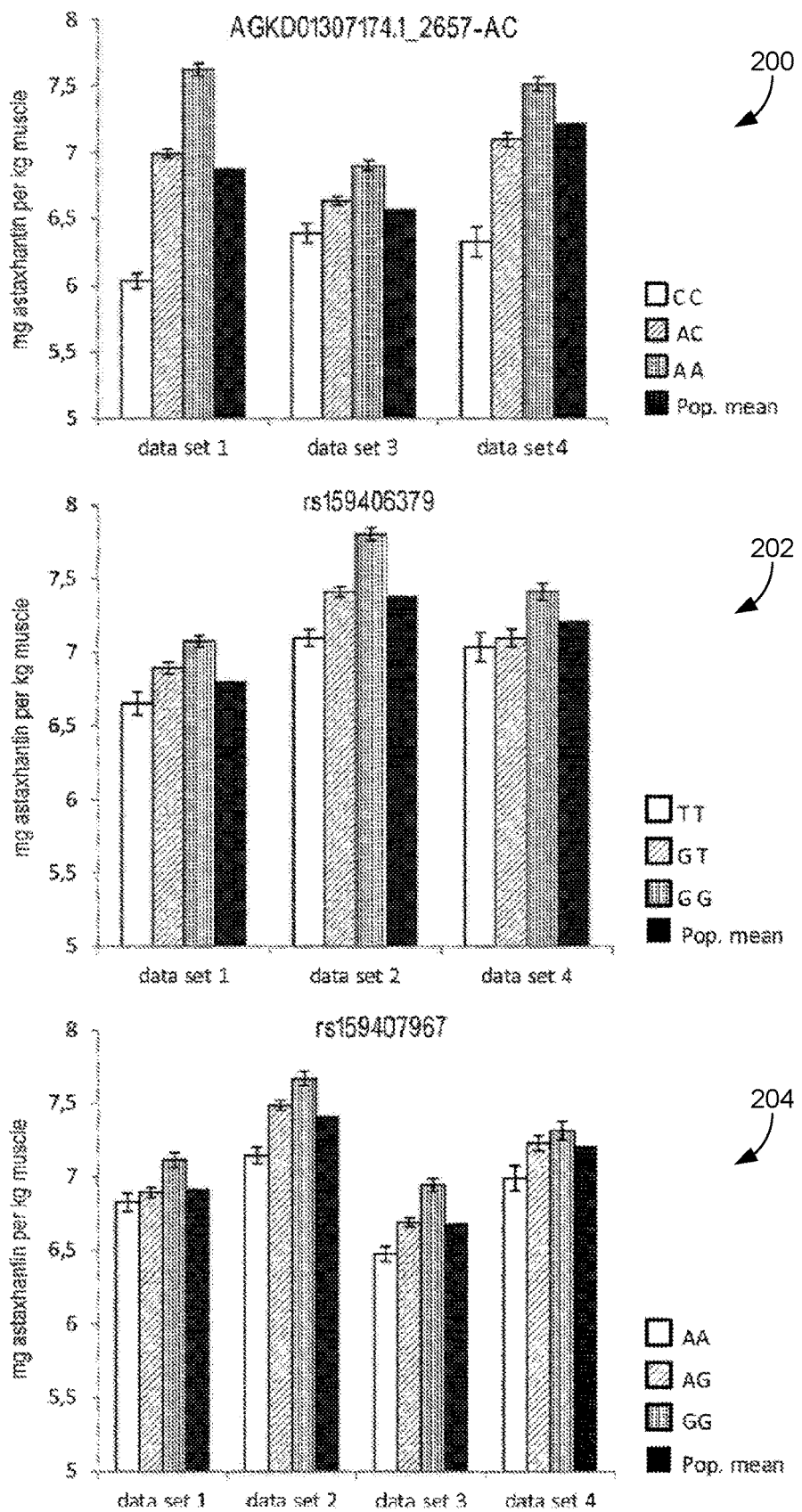
FIG. 2 illustrates how the use of the present invention would lead to an increased ability to utilise dietary pigment. The three frames of the figure correspond to each of the three polymorphisms AGKD01307174.1_2657-AC (chr26), rs159406379 (chr2), and rs159407967 (chr14). Each frame consists of a bar plot corresponding to one of the data sets that were used for testing the SNP in question (Data Set 1, 2, 3, or 4). Each bar plot displays mean phenotypic values (±standard error of the mean) for fillet pigment, for groups of animals (from the data set in question) having the specified genotypes at the DNA polymorphism in question. The fourth bar within each bar plot corresponds to the mean astaxanthin content (mg astaxanthin per kg muscle) within the data set. The three DNA polymorphisms shown in the figure are representative for the nine DNA polymorphisms being the subject of the application.

The SNPs listed in Table 2 can be used in order to select broodstock whose offspring will have fillets with a red colour intensity which is higher than the mean of the population (from which the parents were derived). For example, one may genotype SNP AGKD01307174.1_2657-AC (SNP 1) in the broodstock candidates in order to select a male and a female which are both homozygous for the red allele (which is A in the case of AGKD01307174.1_2657-AC). All offspring resulting from the mating of these two salmon will be homozygous for the red allele. Likewise, one may create groups of salmon that are all homozygous for the pale allele by mating fish that are homozygous for the paleallele. In order to create groups of heterozygous fish one can mate animals that are homozygous for the red allele with animals that are homozygous for the pale pink allele. FIG. 2 displays the mean astaxanthin levels (±standard error of the mean) of fish that would have resulted from such crossing schemes, in populations similar to the populations corresponding to Sample Sets 1 through 4. As can be seen in FIG. 2, the offspring of two parents homozygous for the red allele have offspring that have a significantly more red fillet colour than offspring resulting from other crosses. As can be seen in FIG. 2, this applies to either of the three DNA polymorphisms AGKD01307174.1_2657-AC, rs 159406379, and rs 159407967, these three DNA polymorphisms being used as representative of the SNPs listed in Table 2 (the other ten DNA polymorphisms in Table 2 would yield similar plots). It is also clear from FIG. 2 that offspring having parents that are both homozygous for the red allele have a red colour intensity that is significantly higher than the mean of the population (this applies to all three DNA polymorphisms and all three data sets). FIG. 2 illustrates that the effect of using these DNA polymorphisms in selection is reproducible, having been replicated in three or four large-scale experiments).

4. Discovery of a Gene Determining Fillet Colour in Atlantic Salmon

The analysis of Data Set 1 revealed that many of the SNPs most strongly associated with fillet colour were located on chromosome 26. Two such fillet colour-associated SNPs, located on chromosome 26, were rs 159403576 and rs 159403150. These two SNPs were found to be located in the vicinity of two genes whose biological functions were possibly relevant in the context of fillet colour. One of these two genes were Beta-Carotene 15,15'-Monooxygenase 1 (bcmo1), the other gene coded for a protein similar to bcmo1, so that the gene is termed bcmo1-like (the protein products of the two genes are referred to as Bcmo1 and Bcmo1-like). Alignment of whole-genome Illumina (HiSeq2000) reads from 74 AquaGen animals revealed a number of additional SNPs in the vicinity of the two genes. Ninety-six such SNPs were tested for association to fillet colour, using Data Set 3. The two most significant SNPs, AGKD01307174.1_2657-AC and AGKD01018473.1_11330-CT, were located in or close to the 5' untranslated region of bcmo1-like.

In several different species, Bcmo1 has been shown to be capable of oxidatively cleaving beta-carotene. The applicants have shown that Atlantic salmon Bcmo1 and Bcmo1-like (the versions of these proteins coded for by genes located on Atlantic salmon chromosome 26) are also capable of cleaving beta-carotene. This was done following this procedure: The complete reading frame of both genes, stretching from (and including) the transcriptional start codons to the last amino acid of the protein, was PCR-amplified using cDNA as template. PCR fragments were purified and ligated into a His-Tagged expression vector (pBAD ThioFusion, Life sciences). After plasmid purification the respective plasmids were transformed into a beta-carotene-producing strain of E. coli. Testing of beta-carotene cleavage was carried out in cultures grown at 24° C., whereupon the bacteria were centrifuged and the color of the pellet compared visually.

Neither AGKD01307174.1_2657-AC nor AGKD01018473.1_11330-CT give rise to an amino-acid shift, neither within bcmo1 nor within bcmo1-like. Furthermore, using quantitative Real-Time PCR (qPCR) the applicants have shown that there is no significant difference in expression levels, at either of the two genes, between animals homozygous for the two different alleles at either AGKD01307174.1_2657-AC or AGKD01018473.1_11330-CT. However, the applicants have found that AGKD01307174.1_2657-AC is located within a typical microRNA (miRNA) binding site. MicroRNAs are known to be involved in negative regulation of enzyme activity, acting through different mechanisms such as transcript degradation and translational suppression. It is therefore possible that AGKD01307174.1_2657-AC is a functional mutation which facilitates an increase in the red colour intensity by preventing the binding of a miRNA to bcmo1-like, thus reducing the oxidative cleavage of carotenoids facilitated by bcmo1-like.

The full-length cDNA-sequence of the bcmo1-like gene has GenBank identifier HF443833.1. SNP1 lies within the 3' untranslated region of bcmo1-like, while SNP2 lies 2.38 kb downstream from the last exon of bcmo1-like.

5. Validation Experiment 2014

In 2014, a sample set was collected, similar to Sample Sets 1-3. The sample set from 2014 will be referred to as Sample Set 4. Similar to Sample Sets 1-3, Sample Set 4 consisted of Atlantic salmon from the breeding nucleus of AquaGen; more precisely, the grandparents of the individuals of Sample Set 4 were siblings of the grandparents of the individuals of Sample Set 3. The astaxhantin content of individuals of Sample Set 4 was recorded using Near-Infrared Spectroscopy (instrument: Foss XDS). The measurements were made at a mean body weight of 2636 gram. Sample Set 4 was genotyped using a custom Axiom array from Affymetrix, hereafter referred to as the 56k-chip. The 56k-chip contained 56,177 SNPs. Of the SNPs on the 56k-chip, 3719 were novel, i.e. not on the SNP chips used for genotyping Sample Sets 1-3. The technical details of genotyping of Sample Set 4 were identical to the technical details pertaining to Sample Set 3. The statistical testing for association between individual SNPs and astaxhantin content was performed as described for Sample Sets 1-3. The results from the GWAS on Sample Set 4 were in agreement with the results obtained from Sample Sets 1-3, in the sense that chromosomes 26 and 2 were the ones that harboured the SNPs most strongly associated to fillet colour. The additional, fillet-colour-associated SNPs emerging from the validation experiment were all located on chromosomes 2 or 26, having individual p-values below 0.0005.

REFERENCES

Baldán A, Tarr P, Lee R, and Edwards P A (2006) ATP-binding cassette transporter G1 and lipid homeostasis. Curr Opin Lipidol. 17:227-32.

Davidson W S, Koop B F, Jones S J M, Iturra P, Vidal R. et al. (2010) Sequencing the genome of the Atlantic salmon (*Salmo salar*). Genome Biology 11: 403.

Ferrucci L, Perry J R B, Matteini A, Perola M, Tanaka T et al. (2009) Common variation in the beta-carotene 15,15'-monooxygenase 1 gene affects circulating levels of carotenoids: A genome-wide association study. American Journal of Human Genetics 84: 123-133.

Hendrickson S J, Hazra A, Chen C, Eliassen A H, Kraft P et al. (2012) β-Carotene 15,15'-monooxygenase 1 single nucleotide polymorphisms in relation to plasma carotenoid and retinol concentrations in women of European descent. American Journal of Clinical Nutrition 96:1379-1389.

Industry Standards for Fish (1999) Standard for quality grading of farmed salmon, Industry standard NBS 10-01; http://fhl.nsp01cp.nhosp.no/files/Quality_grading_of_farmed_salmon.pdf Jlali M, Graulet B, Chauveau-Duriot B, Chabault M, Godet E et al. (2012) A mutation in the promoter of the chicken β,β-carotene 15,15'-monooxygenase 1 gene alters xanthophyll metabolism through a selective effect on its mRNA abundance in the breast muscle. Journal of Animal Science 90:4280-4288.

Le Bihan-Duval E, Nadaf J, Berri C, Pitel F, Graulet B et al. (2011) Detection of a cis eQTL controlling BCMO1 gene expression leads to the identification of a QTG for chicken breast meat color. Plos One 6.

Lien S, Gidskehaug L, Moen T, Hayes B J, Berg P R, Davidson W S et al. (2011) A dense SNP-based linkage map for Atlantic salmon (*Salmo salar*) reveals extended chromosome homeologies and striking differences in sex-specific recombination patterns. BMC Genomics 12: 615.

Lietz G, Lange J, and Rimbach G (2010) Molecular and dietary regulation of beta,beta-carotene 15,15'-monooxygenase 1 (BCMO1). Archives of Biochemistry and Biophysics 502:8-16.

Telbisz Á, Özvegy-Laczka C, Hegedűs T, Váradi A, and Sarkadi B. (2013) Effects of the lipid environment, cholesterol and bile acids on the function of the purified and reconstituted human ABCG2 protein. Biochem J. 450: 387-95.

Uimari P, Kontkanen O, Visscher P M, Pirskanen M, Fuentes R, and Salonen J T (2005) Genome-wide linkage disequilibrium from 100,000 SNPs in the East Finland Founder population. Twin Research and Human Genetics 8: 185-197.

---

The invention claimed is:

1. A method of detecting one or more alleles in a salmon, the method comprising:
   a) obtaining a nucleic acid sample from a salmon; and
   b) assaying the nucleic acid sample to detect a presence of one or more alleles in the nucleic acid sample;
   c) detecting the presence of cytosine at position 36 of SEQ ID NO: 14 or cytosine at position 36 of SEQ ID NO: 15.

2. A method of breeding a salmon, the method comprising:
   a) obtaining a nucleic acid sample from a salmon;
   b) assaying the nucleic acid sample to detect a presence of one or more red alleles in the nucleic acid sample,
   c) detecting the presence of an adenine at position 36 of SEQ ID NO: 1 or a thymine at position 36 of SEQ ID NO: 2; and
   d) breeding the salmon.

3. The method of claim 1, wherein the method further comprises:
   detecting the presence of adenine at position 36 of SEQ ID NO: 1 or a thymine at position 36 of SEQ ID NO: 2; and
   breeding the salmon.

4. A method of breeding salmon, the method comprising breeding a salmon, wherein the salmon has an adenine at position 36 in SEQ ID NO: 1; and wherein a sample from the salmon has been tested to detect the presence of an adenine at position 36 in SEQ ID NO: 1 or wherein the salmon has a thymine at position 36 SEQ ID NO: 2; and wherein a sample from the salmon has been tested to detect the presence of an thymine at position 36 in SEQ ID NO: 2.

5. A method of detecting at least one allele present in a DNA polymorphism in salmon, the method comprising:
   a) obtaining a sample from an salmon;
   b) extracting DNA from said sample;
   c) providing an allele-specific polynucleotide that hybridizes to either allele #1 or allele #2 of the DNA polymorphism;
   d) hybridizing the allele-specific polynucleotide to the extracted DNA;
   e) detecting the presence of allele #1 or allele #2 of the DNA polymorphism based on the hybridization of the allele-specific polynucleotide to the extracted DNA, wherein the DNA polymorphism is:
   i) rs 159406379 and: allele #1 is a guanine at position 36 in SEQ ID NO. 6; and allele #2 is a thymine at position 36 in SEQ ID NO. 19; or
   (ii) rs 159407967 and: allele #1 is a guanine at position 36 in SEQ ID NO. 8; and allele #2 is a adenine at position 36 in SEQ ID NO. 21; and
   f) breeding the salmon.

6. A method of breeding a salmon, the method comprising:
   a) obtaining a nucleic acid sample from a salmon;
   b) assaying the nucleic acid sample to detect a presence of one or more red alleles in the nucleic acid sample;
   c) detecting the presence of a guanine at position 36 of SEQ ID NO: 8 or a guanine at position 36 of SEQ ID NO: 6; and
   d) breeding the salmon.

7. A method of breeding salmon, the method comprising breeding a salmon, wherein: (i) the salmon has an guanine at position 36 in SEQ ID NO. 6; and wherein a sample from the salmon has been tested to detect the presence of an guanine at position 36 in SEQ ID NO:6; or (ii) the salmon has an guanine at position 36 in SEQ ID NO. 8; and wherein a sample from the salmon has been tested to detect the presence of a guanine at position 36 in SEQ ID NO:8.

* * * * *

SEQUENCE LISTING

```
<160> NUMBER OF SEQ ID NOS: 26

<210> SEQ ID NO 1
<211> LENGTH: 70
<212> TYPE: DNA
<213> ORGANISM: Atlantic salmon

<400> SEQUENCE: 1
ttgccctcta caatgttaag gtacaatcct gccctatgct ggttatgtca gttggtgctc    60
tgtgtgggaa                                                            70

<210> SEQ ID NO 2
<211> LENGTH: 72
<212> TYPE: DNA
<213> ORGANISM: Atlantic salmon

<400> SEQUENCE: 2
agatgatcac tgcaaaatgt tcaagtttta tatcatattt tgctatttac atttactgtg    60
catgagaagc ca                                                         72

<210> SEQ ID NO 3
<211> LENGTH: 70
<212> TYPE: DNA
<213> ORGANISM: Atlantic salmon

<400> SEQUENCE: 3
ttcttatcaa aacaaaaata agtctggttg gaggagcatt tctttgtggg tttttttggga   60 ggtcattgag                                                            70

<210> SEQ ID NO 4
<211> LENGTH: 70
<212> TYPE: DNA
<213> ORGANISM: Atlantic salmon
```

```
<400> SEQUENCE: 4
tttcccatgg gagaagggggg agcaacacta acaatcatac caactgatct taacgttttt      60
ctagtttttc                                                               70

<210> SEQ ID NO 5
<211> LENGTH: 70
<212> TYPE: DNA
<213> ORGANISM: Atlantic salmon

<400> SEQUENCE: 5
gctttcatat atttaagatt tgaggaccat gtaaaacaat ctcaccatca tcctctcctt       60
ctccattggg                                                               70

<210> SEQ ID NO 6
<211> LENGTH: 70
<212> TYPE: DNA
<213> ORGANISM: Atlantic salmon

<400> SEQUENCE: 6
acacgcgaca gccccgtcac tccgcagctg ggtcggaacc gtaggaacgg tctccacgac       60
gtcgacctga                                                               70

<210> SEQ ID NO 7
<211> LENGTH: 65
<212> TYPE: DNA
<213> ORGANISM: Atlantic salmon

<400> SEQUENCE: 7
attccatttg ctactgacag ctttcttggt tgccaaggtg atgaatccta tacctatacc       60
atatc                                                                    65

<210> SEQ ID NO 8
<211> LENGTH: 70
<212> TYPE: DNA
<213> ORGANISM: Atlantic salmon

<400> SEQUENCE: 8
gtaaaacaat caatcattta tctgtgcttt tactcgtcca gtttgatgcc aatgcagttg       60
gaggaaagga                                                               70

<210> SEQ ID NO 9
<211> LENGTH: 70
<212> TYPE: DNA
<213> ORGANISM: Atlantic salmon
<220> FEATURE:
<221> NAME/KEY: misc_feature
<222> LOCATION: (30)..(30)
<223> OTHER INFORMATION: n is a, c, g, or t

<400> SEQUENCE: 9
tggatactga gtcacggttt taaaagcctn tcatgtgctc tctccgtttg cagagcactt       60
gtgatggtct                                                               70

<210> SEQ ID NO 10
<211> LENGTH: 71
<212> TYPE: DNA
<213> ORGANISM: Atlantic salmon

<400> SEQUENCE: 10
```

-continued

```
atgcagtttg ggctgggttt ttggttgttt ttccagttag tattttcttg aacttatgag    60
tgcatctatg c                                                         71

<210> SEQ ID NO 11
<211> LENGTH: 70
<212> TYPE: DNA
<213> ORGANISM: Atlantic salmon

<400> SEQUENCE: 11
ttgtcctcat tccaggacag ctgttgattc accaaccttt tctccattta gtccgcacta    60
ccggccgcca                                                           70

<210> SEQ ID NO 12
<211> LENGTH: 70
<212> TYPE: DNA
<213> ORGANISM: Atlantic salmon

<400> SEQUENCE: 12
gtattggatt cattagggct gggtgtctgt gatgcgttgt tttgattccc ccacttgtct    60
tctggacaaa                                                           70

<210> SEQ ID NO 13
<211> LENGTH: 70
<212> TYPE: DNA
<213> ORGANISM: Atlantic salmon

<400> SEQUENCE: 13
aagacaagta gtagtcttta ctagattatg tttaagtcaa caaaatgtgt cttacattta    60
caaaaagcct                                                           70

<210> SEQ ID NO 14
<211> LENGTH: 70
<212> TYPE: DNA
<213> ORGANISM: Atlantic salmon

<400> SEQUENCE: 14
ttgccctcta caatgttaag gtacaatcct gccctctgct ggttatgtca gttggtgctc    60
tgtgtgggaa                                                           70

<210> SEQ ID NO 15
<211> LENGTH: 72
<212> TYPE: DNA
<213> ORGANISM: Atlantic salmon

<400> SEQUENCE: 15
agatgatcac tgcaaaatgt tcaagtttta tatcacattt tgctatttac atttactgtg    60
catgagaagc ca                                                        72

<210> SEQ ID NO 16
<211> LENGTH: 70
<212> TYPE: DNA
<213> ORGANISM: Atlantic salmon

<400> SEQUENCE: 16
ttcttatcaa aacaaaaata agtctggttg gaggaacatt tctttgtggg ttttttggga    60
ggtcattgag                                                           70

<210> SEQ ID NO 17
<211> LENGTH: 70
```

```
<212> TYPE: DNA
<213> ORGANISM: Atlantic salmon

<400> SEQUENCE: 17
tttcccatgg gagaaggggg agcaacacta acaattatac caactgatct taacgttttt      60
ctagttttc                                                              70

<210> SEQ ID NO 18
<211> LENGTH: 70
<212> TYPE: DNA
<213> ORGANISM: Atlantic salmon

<400> SEQUENCE: 18
gctttcatat atttaagatt tgaggaccat gtaaagcaat ctcaccatca tcctctcctt      60
ctccattggg                                                             70

<210> SEQ ID NO 19
<211> LENGTH: 70
<212> TYPE: DNA
<213> ORGANISM: Atlantic salmon

<400> SEQUENCE: 19
acacgcgaca gccccgtcac tccgcagctg ggtcgtaacc gtaggaacgg tctccacgac      60
gtcgacctga                                                             70

<210> SEQ ID NO 20
<211> LENGTH: 65
<212> TYPE: DNA
<213> ORGANISM: Atlantic salmon

<400> SEQUENCE: 20
attccatttg ctactgacag ctttcttggt tgacaaggtg atgaatccta tacctatacc      60
atatc                                                                  65

<210> SEQ ID NO 21
<211> LENGTH: 70
<212> TYPE: DNA
<213> ORGANISM: Atlantic salmon

<400> SEQUENCE: 21
gtaaaacaat caatcattta tctgtgcttt tactcatcca gtttgatgcc aatgcagttg      60
gaggaaagga                                                             70

<210> SEQ ID NO 22
<211> LENGTH: 70
<212> TYPE: DNA
<213> ORGANISM: Atlantic salmon
<220> FEATURE:
<221> NAME/KEY: misc_feature
<222> LOCATION: (30)..(30)
<223> OTHER INFORMATION: n is a, c, g, or t

<400> SEQUENCE: 22
tggatactga gtcacggttt taaaagcctn tcatgcgctc tctccgtttg cagagcactt      60
gtgatggtct                                                             70

<210> SEQ ID NO 23
<211> LENGTH: 71
<212> TYPE: DNA
<213> ORGANISM: Atlantic salmon
```

-continued

```
<400> SEQUENCE: 23
atgcagtttg ggctgggttt ttggttgttt ttccatttag tattttcttg aacttatgag     60
tgcatctatg c                                                          71

<210> SEQ ID NO 24
<211> LENGTH: 70
<212> TYPE: DNA
<213> ORGANISM: Atlantic salmon

<400> SEQUENCE: 24
ttgtcctcat tccaggacag ctgttgattc accaatcttt tctccattta gtccgcacta     60
ccggccgcca                                                            70

<210> SEQ ID NO 25
<211> LENGTH: 70
<212> TYPE: DNA
<213> ORGANISM: Atlantic salmon

<400> SEQUENCE: 25
gtattggatt cattagggct gggtgtctgt gatgcattgt tttgattccc ccacttgtct     60
tctggacaaa                                                            70

<210> SEQ ID NO 26
<211> LENGTH: 70
<212> TYPE: DNA
<213> ORGANISM: Atlantic salmon

<400> SEQUENCE: 26
aagacaagta gtagtcttta ctagattatg tttaaatcaa caaatgtgt cttacattta      60 caaaaagcct                                                            70
```